United States Patent [19]

Eng et al.

[11] 4,389,325

[45] Jun. 21, 1983

[54] CHLOROISOCYANURATE COMPOSITIONS

[75] Inventors: Clifford D. Eng, University City; James W. Gambell; Henry K. Yuen, both of St. Louis, all of Mo.

[73] Assignee: Monsanto Company, St. Louis, Mo.

[21] Appl. No.: 342,039

[22] Filed: Jan. 25, 1982

[51] Int. Cl.$^3$ .............................................. C11D 7/54
[52] U.S. Cl. .............................. 252/186.35; 252/95; 252/97; 252/99; 252/187.34
[58] Field of Search .................... 252/186.35, 187.34, 252/95, 97, 99

[56] References Cited

U.S. PATENT DOCUMENTS

| | | | |
|---|---|---|---|
| 3,061,549 | 10/1962 | Dickey | 252/90 |
| 3,352,785 | 11/1967 | Corliss et al. | 252/186.35 |
| 3,364,146 | 1/1968 | Casey et al. | 252/99 |
| 3,816,320 | 6/1974 | Corliss | 252/186.35 |
| 4,116,851 | 9/1978 | Rupp et al. | 252/187.34 |
| 4,149,988 | 4/1979 | Brennan et al. | 252/187 |

*Primary Examiner*—Irwin Gluck
*Attorney, Agent, or Firm*—Jon H. Beusen; James C. Logomasini; Arnold H. Cole

[57] ABSTRACT

The concentration of chlorine-containing compounds in a gaseous mixture in contact with a solid chloroisocyanurate can be safely lowered by use of a porous crystalline alumino-silicate having an essentially uniform pore size and a free aperture dimension of at least about 3.5 angstroms, said alumino-silicate being essentially unreactive with the chloroisocyanurate and its hydrolysis and decomposition products.

16 Claims, No Drawings

CHLOROISOCYANURATE COMPOSITIONS

BACKGROUND OF THE INVENTION

This invention is concerned with chloroisocyanurates selected from the group consisting of trichloroisocyanuric acid, dichloroisocyanuric acid, and the alkali metal salts of dichloroisocyanuric acid. Such isocyanurates are manufactured in substantial quantities for various uses, e.g. as sanitizing and bleaching agents which release available chlorine in aqueous media.

Normally, such isocyanurates are manufactured, shipped and/or stored under conditions that include the presence of small amounts of water (e.g. water vapor in the air) and this water, which may become partly entrained in and/or adsorbed on particles of the isocyanurate, tends to react slowly with the isocyanurate liberating, over an extended time, various hydrolysis and decomposition products including, e.g. HCl, $Cl_2$, HOCl, $NH_2Cl$, $Cl_2O$, $NHCl_2$ and $NCl_3$. Even in the absence of water, heat may cause some decomposition of these compounds.

Because of their strong oxidizing potential, such isocyanurates are generally shipped and stored in closed (gas-tight) containers, e.g. drums. Hydrolysis and decomposition of the isocyanurates in such containers are highly temperature dependent and under warm weather conditions, the concentration of chlorine-containing hydrolysis and/or decomposition products in the vapor space within such containers can rise to undesirable levels. Accordingly, the desirability of techniques for lowering that concentration has been recognized.

For example, U.S. Pat. No. 3,061,549 issued Oct. 30, 1962 to M. L. Dickey disclosed that decomposition products of di- and trichloroisocyanuric acid can be converted to compounds having no objectionable odor by reaction with various "deodorant" materials. However, as shown hereinafter, the potential for reaction of such materials with the chloroisocyanuric acids can present a substantial danger of fire or explosion. Moreover, merely converting the decomposition products to non-odorous compounds may not render them safe.

In another approach to the problem, U.S. Pat. No. 4,149,988 issued Apr. 17, 1979 to J. P. Brennan recognizes the desirability of inhibiting decomposition of the chloroisocyanurates using compounds which are unreactive therewith and insensitive to moisture, and discloses that such a result can be obtained using alkaline earth metal sulfates. However, as also shown hereinafter, such sulfates are not effective with mixtures containing higher concentrations of chlorine-containing compounds.

In the absence of an adequate solution to this problem, it is an object of this invention to provide a technique useful in lowering the concentration of chlorine-containing compounds in a gaseous mixture in contact with such a chloroisocyanurate and, additionally, to prevent the accumulation of such compounds therein. In view of the great reactivity of the chloroisocyanurates, it is desirable that such a technique can be carried out using materials which are essentially unreactive with the chloroisocyanurates and with products of their decomposition and/or hydrolysis.

Another object of the invention is to use a material which will achieve and maintain those results over extended periods of time, and under adverse conditions including elevated temperatures. Another object is to use a material which is stable against chemical attack by the chloroisocyanurates and their decomposition and hydrolysis products, and by water so that such a material does not lose its effectiveness due to such attack. A further object is to use a material that is innocuous to personnel and equipment, easy to handle and of reasonable cost.

SUMMARY OF THE INVENTION

It has been found that the foregoing objects can be achieved by use of porous crystalline aluminosilicates which have an essentially uniform pore size and are essentially unreactive with the chloroisocyanurates and their decomposition/hydrolysis products as determined by accelerating rate calorimetry. Preferably, these alumino-silicates have a free aperture dimension of at least about 3.5 angstroms.

Accordingly, the invention provides a novel composition comprising a solid chloroisocyanurate selected from the group mentioned hereinbefore, and such a porous alumino-silicate. Also provided is a method for lowering the concentration of chlorine-containing compounds in a gaseous mixture in contact with such a chloroisocyanurate by disposing such an alumino-silicate in contact with that gaseous mixture.

DETAILED DESCRIPTION OF THE INVENTION

The compositions of this invention contain trichloroisocyanuric acid, dichloroisocyanuric acid (anhydrous or the monohydrate), an alkali metal (usually sodium or potassium) salt of dichloroisocyanuric acid, or a mixture of two or more of such acids. Especially good results are obtained in embodiments comprising trichloroisocyanuric acid. The chloroisocyanurate may be present in any solid form, but is most commonly finely divided, e.g. powdered or granulated.

The invention is used most advantageously when such compositions contain water in an amount tending to react with the chloroisocyanurate producing normally-gaseous hydrolysis products such as, for example, HCl, $Cl_2$, HOCl, $Cl_2O$, $NHCl_2$, $NH_2Cl$ and $CNl_3$. Even minuscule quantities of water, e.g. those entrained in or adsorbed on particles of the chloroisocyanurate during manufacture, packaging or storage, are typically sufficient to result in some measurable hydrolysis. In the gas-tight containers conventionally used to transport and store such compositions, the concentration of such hydrolysis products and other products of decomposition of the chloroisocyanurate in the vapor space therein (expressed as the weight percent of $Cl_2$ equivalent to the chlorine in such products) can rise as high as 10%, or even substantially higher under especially adverse conditions including high ambient temperatures.

Desirably, that concentration is lowered to no more than about 5%. More desirably, and especially for purposes of worker safety and comfort, that concentration is lowered to no more than about 1% and, especially advantageously, to not more than about 0.5%. Equally important, that concentration is desirably lowered rapidly and maintained at such low levels for extended periods of time, e.g. up to about six months, a year or even longer.

The alumino-silicates used in this invention are essentially unreactive below 80° C. with the chloroisocyanurate and products of hydrolysis and decomposition thereof as determined by accelerating rate calorimetry which, for purposes of this invention, meas an essentially adiabatic procedure carried out with the apparatus and procedure described in *Accelerating Rate Calorimeter Operating Manual,* Columbia Scientific Industries, CSI Part No. 851-9001, and Townsend, D. I. and Tow, J. C., 37 *Thermochim Acta* 1-30 (1980) using a mixture of the chloroisocyanurate and the alumino-silicate or alternative material.

The alumino-silicates used herein have an aperture dimension (diameter or, if the apertures are not essentially round, the larger of two dissimilar dimensions) of at least about 3.5 angstroms, preferably at least about 5 angstroms, and even more preferably at least about 7 angstroms. Although other aluminosilicates having smaller aperture dimensions may provide satisfactory results over short periods of time and/or with low gas-phase chlorine concentrations, presumably by external adsorption of water and/or and aforementioned products of decomposition of hydrolysis, it is an important discovery of this invention that good results are obtainable much more rapidly and maintained for much longer periods of time using the alumino-silicates described herein.

It is also preferred that the alumino-silicates be dehydrated, i.e., not fully hydrated. In fact, superior results are generally achieved when the alumino-silicate has had most (preferably essentially all) of its water of hydration removed, e.g. by heat.

Although alumino-silicates that are amorphous and/or naturally formed (with or without refinement) can provide satisfactory results in some instances, more attractive embodiments of the invention utilize crystalline alumino-silicates, and most desirably the synthetic crystalline alumino-silicates of essentially uniform pore size. The invention can be carried out using metal forms of such alumino-silicates, e.g. those containing one or more alkali metals, one or more alkaline earth metals, or a combination thereof. In other embodiments, alumino-silicates essentially devoid of such metals can be used.

In a highly preferred embodiment, the invention is carried out using synthetic crystalline alumino-silicate of the commercially available variety known as "molecular sieves" because of the great uniformity of size of their aperture dimensions. Particularly useful in this invention are the following alumino-silicates of that kind manufactured by the Linde Division of Union Carbide Corporation or the Norton Company (Division of Combustion Engineering).

| Designation ("Type") | Chemical Formula* |
|---|---|
| Linde 4A | $Na_{12}[(AlO_2)_{12}(SiO_2)_{12}] \cdot xH_2O$ |
| Linde 5A | $Ca_{4.5}Na_3[(AlO_2)_{12}(SiO_2)_{12}] \cdot xH_2O$ |
| Norton 10Na | $Na_8[(AlO_2)_8(SiO_2)_{40}] \cdot xH_2O$ |
| Norton 10H | (Hydrogen form of 10Na) |
| Linde 13X | $Na_{86}[(AlO_2)_{86}(SiO_2)_{106}] \cdot xH_2O$ |
| Linde 13Y | $Na_{56}[(AlO_2)_{56}(SiO_2)_{136}] \cdot xH_2O$ |

*(x is a number substantially less than that corresponding to full hydration.)

A surprising advantage of the use of these alumino-silicates in the present invention is that, although crystalline alumino-silicates are generally believed stable in aqueous media having pH's only between 5 and 12, the aforementioned molecular sieves have shown excellent stability in the compositions of this invention containing chloroisocyanurates whose aqueous solutions are highly acidic, e.g. a pH of 2.3–2.5 for a 1% solution of trichloroisocyanuric acid.

Additional information concerning the alumino-silicates used in this invention can be found in *Zeolite Molecular Sieves* by D. C. Breck, John Wiley & Sons, New York, N.Y. (1974) and *Natural Zeolites-Occurrence, Properties, Use,* a collection of papers presented at Tucson, Ariz. in June, 1976, edited by L. B. Sand and F. A. Mumpton, Pergamon Press, Oxford, Great Britain (1st Ed. 1978), the disclosures of which are incorporated herein by reference.

The invention can be carried out using any proportion of the alumino-silicate sufficient to substantially lower the concentration of chlorine in a gaseous mixture of contact (e.g. equilibrium) with the chloroisocyanurate. The specific amount of alumino-silicate desired is a function of the potential of the chloroisocyanurate to undergo hydrolysis and/or decomposition, and the length of time and conditions (e.g. temperature) under which the alumino-silicate is to remain effective. Based on the weight of the chloroisocyanurate, at least about 0.1% of alumino-silicate is sufficient in some instances; normally between about 0.15% and about 1.5% of alumino-silicate is preferred, while in some cases up to about 3% or more will be advantageous.

In this invention, the alumino-silicates are most commonly employed out of direct contact with the chloroisocyanurate, but in contact with a gaseous mixture which is in contact with the chloroisocyanurate, e.g. a vapor space above the chloroisocyanurate in a gas-tight storage or shipping container. However, at normally encountered conditions (e.g. temperatures) such alumino-silicates remain safe and effective despite direct contact between the alumino-silicate and the chloroisocyanurate, whether such contact is accidental or by design.

This is attributable to another important advantage of the invention, which is that the prescribed alumino-silicates do not pose a rick under normally encountered shipping and storage conditions of a dangerous reaction with the chloroisocyanurate, and thus can be used in such compositions over a wide range of temperatures. As shown hereinafter, the danger of such a reaction, leading to explosion and/or fire, is a major disadvantage of the use of materials suggested by the prior art for similar purposes. A related advantage of the alumino-silicates used herein is that they are reusable after simple reconditioning (usually only dehydration by heat) and, ultimately, they are safe for disposal.

The following specific examples are intended to illustrate the invention and do not imply any limitations on its scope. In this disclosure temperatures are in Centigrade and percentages and proportions are by weight, except where otherwise noted.

EXAMPLES 1–12

Several porous alumino-silicates of the Linde "molecular sieve" variety described herein were tested for their ability to maintain a low percent chlorine in the vapor space inside commercial drums of a granulated trichloroisocyanuric acid. Each drum contained 770 kg of the acid and had a volume of 120 liters, 20 liters of which was occupied by a vapor space above the acid. In each test the indicated amount of alumino-silicate was placed in a gas-permeable, acid-resistant bag placed on the acid inside the drum. After storage for six days at an average temperature of 20°, the drums were opened and gas samples taken from the vapor space of each were analyzed by amperometric titration for chlorine. Results were as follows:

TABLE I

| Example | Sieve Type | Wt. Sieve Based On Acid, % | % Cl$_2$ |
|---|---|---|---|
| 1 | 13X | 0.07 | 0.7 |
| 2 | 13X | 0.14 | <0.5 |
| 3 | 13X | 0.29 | <0.5 |
| 4 | 13X | 0.57 | <0.5 |
| 5 | 5A | 0.07 | 0.8 |
| 6 | 5A | 0.14 | <0.5 |
| 7 | 5A | 0.29 | <0.5 |
| 8 | 5A | 0.57 | <0.5 |
| 9 | 4A | 0.07 | 1.2 |
| 10 | 4A | 0.14 | <0.5 |
| 11 | 4A | 0.29 | <0.5 |
| 12 | 4A | 0.57 | <0.5 |
| A | None | — | 3.1 (Avg.) |

EXAMPLES 13-15

Similarly, drums of a granulated trichloroisocyanuric acid were placed in extended plant storage at temperatures which varied between −2° and 31° and averaged about 14°. Periodically the drums were opened and vapor samples removed for quantitative chlorine analysis, calculated as % Cl$_2$. The alumino-silicate was Linde molecular sieve Type 13X. Results are in Table II.

TABLE II

| Example | Wt. 13X Based On Acid, % | % Cl$_2$ at Day | | | | | | | | |
|---|---|---|---|---|---|---|---|---|---|---|
| | | 4 | 6 | 13 | 20 | 27 | 34 | 42 | 49 | 64 |
| 13 | 0.29 | <0.5 | 0.6 | — | 1.5 | 1.4 | <0.5 | <0.5 | 0.6 | <0.5 |
| 14 | 0.57 | <0.5 | <0.5 | <0.5 | — | <0.5 | → | → | → | → |
| 15 | 1.14 | <0.5 | <0.5 | <0.5 | 1.4 | 1.4 | <0.5 | → | → | → |
| B | None | 8.4 | 5.3 | — | 6.3 | — | — | 1.9 | — | 2.7 |
| C | None | — | — | 7.7 | — | 6.8 | — | — | 3.9 | — |

EXAMPLES 16-18

Another series of tests was run with drums of a granulated trichloroisocyanuric acid in extended plant storage at temperatures which varied between −2° and 29° and averaged about 12°. In this series the performance of Linde molecular sieve Type 13X was compared with equal quantities of activated carbon or a 50:50 mixture of calcium oxide and silica gel. Results are in Table III.

TABLE III

| Example | Material Used | Wt. Mat'l. Based On Acid, % | % Cl$_2$ At Day | | | | | | | | | | |
|---|---|---|---|---|---|---|---|---|---|---|---|---|---|
| | | | 0 | 2 | 3 | 8 | 10 | 17 | 25 | 32 | 39 | 45 | 51 |
| 16 | 13X | 0.14 | — | — | <0.5 | — | <0.5 | 0.9 | 0.7 | <0.5 | 3.4 | 3.5 | 3.4 |
| 17 | 13X | 0.29 | — | — | <0.5 | → | → | → | → | → | → | 0.7 | 0.5 |
| 18 | 13X | 0.57 | — | — | <0.5 | — | 0.7 | <0.5 | → | → | → | → | → |
| D | Activated Carbon and Silica Gel | 0.29 | 3.1 | — | <0.5 | — | 0.6 | — | <0.5 | → | → | → | → |
| E | Activated Carbon and Silica Gel | 0.57 | — | — | <0.5 | — | 1.5 | — | <0.5 | → | → | → | → |
| F | Activated Carbon and Silica Gel | 1.14 | — | — | 0.5 | — | 0.8 | — | <0.5 | → | → | → | — |
| G | CaO | 0.29 | — | 1.9 | — | 1.7 | — | — | — | — | — | — | — |
| H | CaO | 0.57 | — | 1.8 | — | 2.1 | — | 3.1 | — | — | — | — | — |
| I | CaO | 1.14 | — | 0.7 | — | — | 1.1 | 2.3 | 1.8 | — | 1.2 | 1.0 | 0.8 |
| J | None | — | 3.1 | 3.6 | — | — | 5.8 | — | 11.1 | — | — | 13.0 | — |

EXAMPLES 19-30

Another series of tests using a granulated trichloroisocyanuric acid having a higher potential for chlorine evolution was carried out at temperatures varying between 11° and 30° and averaging about 21°. In this series Linde Type 4A or 13X molecular sieve was placed in each drum after storage long enough to establish an equilibrium between the acid and vapor space above it. Results are in Table IV.

TABLE IV

| Example | Sieve Type | Sieve Wt. Based On Acid, % | % Cl$_2$ At Day | | | | | | | | | | |
|---|---|---|---|---|---|---|---|---|---|---|---|---|---|
| | | | 0 | 1 | 5 | 8 | 13 | 18 | 22 | 29 | 42 | 49 | 57 |
| 19 | 4A Pellets | 0.29 | 30 | — | 20 | — | — | — | 18 | — | — | — | — |
| 20 | 4A Pellets | 0.57 | 32 | — | 15 | — | — | — | 15 | — | — | — | — |
| 21 | 4A Pellets | 1.14 | 29 | 9 | 8 | 7 | — | 8 | 8 | — | — | — | — |
| 22 | 4A Powder | 0.29 | 27 | — | 21 | — | — | — | 18 | — | — | — | — |
| 23 | 4A Powder | 0.57 | 32 | — | 16 | — | — | — | 16 | — | — | — | — |
| 24 | 4A Powder | 1.14 | 30 | 5 | 7 | 7 | — | 10 | 10 | — | — | — | — |

TABLE IV-continued

| Example | Sieve Type | Sieve Wt. Based On Acid, % | % Cl$_2$ At Day | | | | | | | | | | |
|---|---|---|---|---|---|---|---|---|---|---|---|---|---|
| | | | 0 | 1 | 5 | 8 | 13 | 18 | 22 | 29 | 42 | 49 | 57 |
| 25 | 13X Powder | 0.29 | 31 | 7 | 15 | 15 | 19 | 15 | 15 | — | — | 12 | — |
| 26 | 13X Powder | 0.57 | 24 | 2 | 5 | 6 | 10 | 10 | 10 | — | 12 | 12 | — |
| 27 | 13X Powder | 1.14 | 25 | 1 | 2 | 2 | 8 | 2 | 2 | 11 | 2 | 3 | 3 |
| 28 | 13X Pellets | 0.29 | 31 | 8 | 14 | 15 | 20 | 17 | 16 | — | — | 16 | — |
| 29 | 13X Pellets | 0.57 | 26 | 3 | 8 | 9 | 14 | 11 | 11 | — | 13 | 12 | — |
| 30 | 13X Pellets | 1.14 | 30 | 1 | 3 | 4 | 5 | 4 | 6 | 4 | 6 | 6 | 6 |

EXAMPLES 31–33

The importance of free aperture dimension was illustrated by the following comparative tests in which several natural alumino-silicates, after being ground to a powder and then dried for 3 hours at 400°, were evaluated for their ability to lower the % Cl$_2$ in a gaseous mixture in equilibrium with a granular trichloroisocyanuric acid maintained at 35°–38° for 3 days. Results obtained using 0.2% alumino-silicate based on the acid were as follows:

TABLE V

| Example | Alumino-Silicate | Free Aperture of Main Channels, Angstroms | % Cl$_2$ |
|---|---|---|---|
| 31 | Chabazite | 3.7 × 4.2 | 0.65 |
| 32 | Phillipsite | 4.2 × 4.4 | 1.13 |
| 33 | Erionite | 3.6 × 5.2 | 0.34 |
| K | Analcime | 2.6 | 2.40 |

SAFETY COMPARISONS

Using accelerating rate calorimetry, an alumino-silicate useful in this invention was compared with other materials for thermal hazards in mixtures with a powdered trichloroisocyanuric acid at temperatures from ambient up to 80°. Results were as follows:

Linde Type 13X Molecular Sieve (pellets; 3 gm acid/gm sieve)—No heat or gas evolution (no hazards).

Norite A Activated Carbon (North American Norite Co.; 3 gm acid/gm carbon)—At room temperature began rapidly self-heating to 170° where self-heating accelerated.

Mixture of 4 parts MgSO$_4$, 2 parts NaHCO$_3$ and 2 parts Activated Carbon (3 gm acid/gm mixture)—Beginning at room temperature, self-heated to 230° where the typical trichloroisocyanuric acid exotherm accelerated heating until the sample cell ruptured.

We claim:

1. A composition comprising a solid chloroisocyanurate selected from the group consisting of trichloroisocyanuric acid, dichloroisocyanuric acid, alkali metal salts of dichloroisocyanuric acid and mixtures thereof, and a porous crystalline alumino-silicate having an essentially uniform pore size and a free aperture dimension of at least about 3.5 angstroms, said alumino-silicate being essentially unreactive below 80° C. with said chloroisocyanurate and hydrolysis and decomposition products thereof as determined by accelerating rate calorimetry.

2. A composition of claim 1 comprising water capable of measurable hydrolysis of said chloroisocyanurate.

3. A composition of claim 1 wherein said alumino-silicate is present in an amount which is at least about 0.1% by weight of said chloroisocyanurate.

4. A composition of claim 1 wherein the formula of said alumino-silicate is essentially Na$_{12}$[(AlO$_2$)$_{12}$-(SiO$_2$)$_{12}$].xH$_2$O or Ca$_{4.5}$Na$_3$[(AlO$_2$)$_{12}$(SiO$_2$)$_{12}$].xH$_2$O.

5. A composition of claim 1 wherein said dimension is at least about 7 angstroms.

6. A composition of claim 5 wherein the formula of said alumino-silicate is essentially Na$_{86}$[(AlO$_2$)$_{86}$-(SiO$_2$)$_{106}$].xH$_2$O or Na$_{56}$[(AlO$_2$)$_{56}$(SiO$_2$)$_{136}$].xH$_2$O.

7. A composition of claim 1 comprising a gaseous mixture in contact with said alumino-silicate and said chloroisocyanurate, said alumino-silicate being present in an amount sufficient to substantially lower the concentration of chlorine in said gaseous mixture.

8. A composition of claim 1 wherein said chloroisocyanurate is trichloroisocyanuric acid.

9. A composition of claim 8 wherein said chloroisocyanurate is finely divided.

10. A method for lowering the concentration of chlorine in a gaseous mixture in contact with a solid chloroisocyanurate selected from the group consisting of trichloroisocyanuric acid, dichloroisocyanuric acid, the alkali metal salts of dichloroisocyanuric acid, and mixtures thereof, said method comprising disposing in contact with said gaseous mixture a porous crystalline alumino-silicate having an essentially uniform pore size and a free aperture dimension of at least about 3.5 angstroms, said alumino-silicate being essentially unreactive below 80° C. with said chloroisocyanurate and hydrolysis and decomposition products thereof as determined by accelerating rate calorimetry.

11. A method of claim 10 wherein said chloroisocyanurate and said gaseous mixture contain water capable of measurable hydrolysis of said chloroisocyanurate.

12. A method of claim 11 wherein said alumino-silicate is disposed in contact with said gaseous mixture in an amount which is at least about 0.1% by weight of said chloroisocyanurate.

13. A method of claim 12 wherein the formula of said alumino-silicate is essentially Na$_{12}$[(AlO$_2$)$_{12}$-(SiO$_2$)$_{12}$].xH$_2$O or Ca$_{4.5}$Na$_3$[(AlO$_2$)$_{12}$(SiO$_2$)$_{12}$].xH$_2$O.

14. A method of claim 13 wherein said dimension is at least about 7 angstroms.

15. A method of claim 12 wherein the formula of said alumino-silicate is essentially Na$_{86}$[(AlO$_2$)$_{86}$-(SiO$_2$)$_{106}$].xH$_2$O or Na$_{56}$[(AlO$_2$)$_{56}$(SiO$_2$)$_{136}$].xH$_2$O.

16. A method of claim 12 wherein said chloroisocyanurate is trichloroisocyanuric acid.

* * * * *